United States Patent
Otterstatter et al.

(10) Patent No.: US 11,324,238 B2
(45) Date of Patent: May 10, 2022

(54) SYSTEM AND METHOD FOR FILTERING BEVERAGES

(71) Applicant: Donaldson Company, Inc., Minneapolis, MN (US)

(72) Inventors: Matthew R. Otterstatter, Eagan, MN (US); Prashant V. Shrikhande, Eden Prairie, MN (US)

(73) Assignee: Donaldson Company, Inc., Bloomington, MN (US)

(*) Notice: Subject to any disclaimer, the term of this patent is extended or adjusted under 35 U.S.C. 154(b) by 0 days.

(21) Appl. No.: 16/952,997

(22) Filed: Nov. 19, 2020

(65) Prior Publication Data

US 2021/0153527 A1 May 27, 2021

Related U.S. Application Data

(60) Provisional application No. 62/938,718, filed on Nov. 21, 2019.

(51) Int. Cl.
*A23L 2/46* (2006.01)
*A23L 2/72* (2006.01)
(Continued)

(52) U.S. Cl.
CPC .................. *A23L 2/74* (2013.01); *A23L 2/02* (2013.01); *A23L 2/087* (2013.01); *A23L 2/46* (2013.01);
(Continued)

(58) Field of Classification Search
CPC .. B01D 61/025; B01D 61/142; B01D 61/145; B01D 61/147; B01D 61/18; B01D 61/58;
(Continued)

(56) References Cited

U.S. PATENT DOCUMENTS

| 4,643,902 A | * | 2/1987 | Lawhon | A23L 2/082 426/271 |
| 5,731,164 A | * | 3/1998 | Becker | A61L 2/022 210/637 |

(Continued)

FOREIGN PATENT DOCUMENTS

| EP | 0137671 | 4/1985 |
| EP | 0174594 | 3/1986 |

(Continued)

OTHER PUBLICATIONS

Cheryan; "Ultrafiltration and Microfiltration Handbook" (1998), CRC Press, ISBN 1420069020, pp. 76-77. (Year: 1998).*

(Continued)

*Primary Examiner* — Magali P Slawski
*Assistant Examiner* — Angel Olivera
(74) *Attorney, Agent, or Firm* — Mueting Raasch Group

(57) ABSTRACT

A method for preparing a filtered beverage includes filtering a raw beverage using a cross-flow ultrafiltration device to produce a solids fraction and a liquid fraction; heating the solids fraction to a temperature of 60° C. or greater to produce a pasteurized solids fraction; microfiltering the liquid fraction through a microfilter having a size cut-off of 1 μm or smaller to produce a microfiltered liquid fraction; and combining the pasteurized solids fraction and the microfiltered liquid fraction to result in the filtered beverage.

19 Claims, 6 Drawing Sheets

(51) Int. Cl.
| | |
|---|---|
| *A23L 2/74* | (2006.01) |
| *A23L 3/005* | (2006.01) |
| *B01D 61/02* | (2006.01) |
| *B01D 61/14* | (2006.01) |
| *B01D 61/18* | (2006.01) |
| *B01D 61/20* | (2006.01) |
| *B01D 61/58* | (2006.01) |
| *B01D 65/10* | (2006.01) |
| *C12H 1/07* | (2006.01) |
| *C12H 1/16* | (2006.01) |
| *C12H 1/18* | (2006.01) |
| *A23L 2/02* | (2006.01) |
| *A23L 2/08* | (2006.01) |
| *A23L 3/48* | (2006.01) |
| *A61L 2/00* | (2006.01) |
| *A61L 2/02* | (2006.01) |
| *A23L 2/10* | (2006.01) |
| *A61L 2/04* | (2006.01) |

(52) U.S. Cl.
CPC .............. *A23L 2/72* (2013.01); *A23L 3/005* (2013.01); *A23L 3/48* (2013.01); *A61L 2/0017* (2013.01); *A61L 2/0023* (2013.01); *A61L 2/022* (2013.01); *B01D 61/025* (2013.01); *B01D 61/142* (2013.01); *B01D 61/145* (2013.01); *B01D 61/147* (2013.01); *B01D 61/18* (2013.01); *B01D 61/58* (2013.01); *B01D 65/10* (2013.01); *C12H 1/16* (2013.01); *C12H 1/18* (2013.01); *A23L 2/082* (2013.01); *A23L 2/10* (2013.01); *A23V 2002/00* (2013.01); *A61L 2/04* (2013.01); *B01D 61/20* (2013.01); *B01D 2311/06* (2013.01); *B01D 2311/2692* (2013.01); *B01D 2315/10* (2013.01); *B01D 2317/022* (2013.01); *B01D 2317/025* (2013.01); *C12H 1/063* (2013.01)

(58) Field of Classification Search
CPC .... B01D 65/10; B01D 61/20; B01D 2311/06; B01D 2311/2692; B01D 2315/10; B01D 2317/025; A23L 2/74; A23L 2/02; A23L 2/46; A23L 3/48; A23L 2/082; A23L 2/087; A23L 2/10; A23L 2/72; A23V 2002/00; A61L 2/0017; A61L 2/0023; A61L 2/022; A61L 2/04; C12H 1/063; C12H 1/18

USPC ......................... 426/495, 521, 599
See application file for complete search history.

(56) References Cited

U.S. PATENT DOCUMENTS

| | | | |
|---|---|---|---|
| 2013/0180917 A1* | 7/2013 | Chu .................. | B01D 67/0088 210/634 |
| 2015/0010683 A1 | 1/2015 | Wu et al. | |
| 2018/0228184 A1 | 8/2018 | Alvarez et al. | |

FOREIGN PATENT DOCUMENTS

| | | |
|---|---|---|
| EP | 3628170 | 4/2020 |
| EP | 3628171 | 4/2020 |
| TW | 201021722 | 6/2010 |
| WO | 2013/096996 | 7/2013 |
| WO | 2013/126662 | 8/2013 |

OTHER PUBLICATIONS

Tetra Pak, "Juice Nectar Stilldrink Processing with aseptic blending", 2020, Tetra Pak International S.A., Pully/Lausanne, Switzerland, 30 pages.

International Patent Application No. PCT/US2020/061320, filed Nov. 19, 2020, International Search Report and Written Opinion dated Mar. 10, 2021, 10 pages.

Mihalev, et al., "Chapter 3: Classification of Fruit Juices", in Fruit Juices, Rajauria, et al., (Ed), Elsevier, London, UK, 2018, pp. 33-44.

Rai, et al., "Clarification of pectin-containing juice using ultrafiltration", May 2009, Current Science, 96(10):1361-1371.

Tetra Pak JNSD Line Concept Product Data Sheet, "The Big Squeeze: Save Water, Save Energy", Tetra Pak International S.A., Pully/Lausanne, Switzerland, 1 page.

Tetra Pak White Paper, "Juice pasteurization—Can we do better?", Tetra Pak International S.A., Pully/Lausanne, Switzerland, 9 pages.

Bates, et al., "Principles and practices of small- and medium-scale fruit juice processing", FAO Agricultural Services Bulletin 146, Food and Agricultural Organizations of the United Nations, Jan. 1, 2001, 221 pages. Retrieved online Mar. 8, 2021. Available on the Internet at https://ucanr.edu/datastoreFiles/234-2085.pdf. Pages where relevant text appears: 56-75.

* cited by examiner

SYSTEM AND METHOD FOR FILTERING BEVERAGES

CROSS REFERENCE TO RELATED APPLICATIONS

This application claims the benefit of U.S. Provisional Application No. 62/938,718, filed 21 Nov. 2019, the disclosure of which is incorporated by reference herein in its entirety.

BACKGROUND

Beverages prepared from fruits, vegetables, and other plant parts, as well as dairy-based beverages, are often processed to reduce microbial load and to improve shelf life. Such processing may include heating (e.g., pasteurization). However, heating the beverages may alter their flavor profile and deteriorate beneficial micronutrients that may be present in the raw (unprocessed) beverages.

An example of a beverage that is commonly pasteurized to increase its shelf life is orange juice. Large scale commercial production of orange juice began in response to the need to provide a vitamin C rich food product to American soldiers during World War II. The first frozen concentrated orange juice product was launched in the late 1940's. While the concentrated juice provided a convenient and affordable source of orange juice to many consumers, the processes used to produce the concentrate caused undesirable changes in the flavor and texture of the juice. Not-from-concentrate ("NFC") orange juice was developed to provide a product with improved flavor and texture. However, even though NFC juice provided an improvement in flavor over concentrated juice, the need to pasteurize the juice to reduce the microbial load still causes degradation of many flavor compounds and other thermally labile compounds, such as vitamin C, in the juice.

Freshly squeezed, unpasteurized juice is becoming more popular among consumers due to its superior flavor. However, without pasteurization or other treatments, the microbial load of the juice significantly reduces its shelf life compared to pasteurized NFC juices.

There is a need to provide a system and method for preparing beverages with a reduced microbial load and increased shelf stability. There is a need to provide a system and method for preparing an NFC juice that has a reduced microbial load and increased shelf stability.

SUMMARY

A method for preparing a filtered beverage includes filtering a raw beverage using a cross-flow ultrafiltration device to produce a solids fraction and a liquid fraction; heating the solids fraction to a temperature of 60° C. or greater to produce a pasteurized solids fraction; microfiltering the liquid fraction through a microfilter having a size cut-off of 1 μm or smaller to produce a microfiltered liquid fraction; and combining the pasteurized solids fraction and the microfiltered liquid fraction to result in the filtered beverage. In some embodiments, the beverage is a fruit or vegetable juice.

A filtration system includes an ultrafiltration device defining an ultrafiltration retentate side and an ultrafiltration permeate side, the ultrafiltration device being configured in cross-flow mode; a heater coupled with and configured to receive flow from the ultrafiltration retentate side and comprising an output line; a microfilter coupled with and configured to receive flow from the ultrafiltration permeate side, the microfilter comprising a microfiltration upstream side and microfiltration filtrate side and having a particle size cut-off of 1 μm or smaller, the microfilter being configured in direct flow filtration mode; and a mixer coupled with and configured to receive flow from the heater output line and the microfiltration filtrate side.

DETAILED DESCRIPTION

Figure 1:
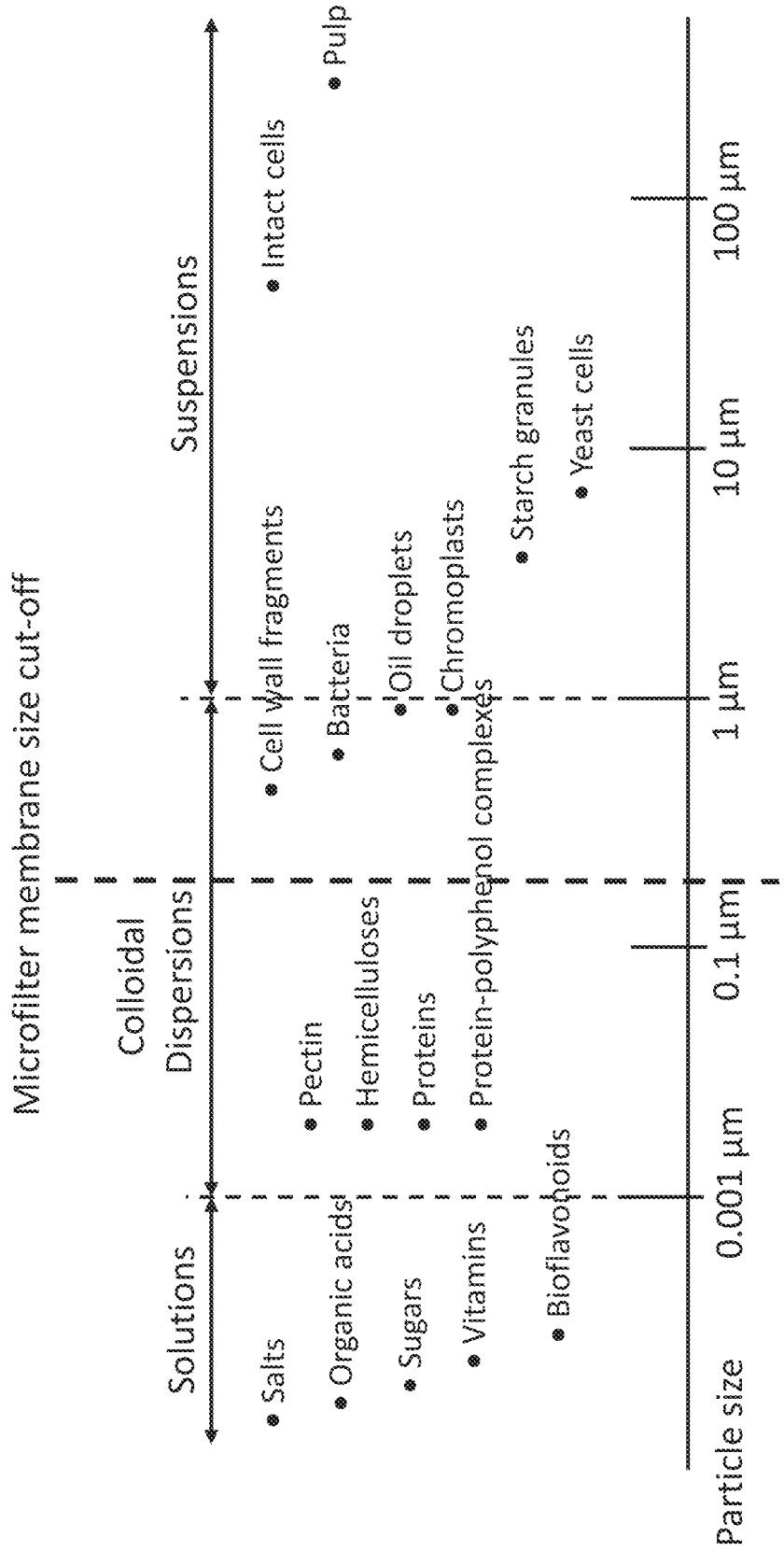
FIG. 1 is graphical representation of the components of orange juice by size.

The present disclosure relates to systems and methods for filtering beverages. In particular, the present disclosure relates to systems and methods for filtering fruit and vegetable juices, such as orange juice, and for producing a not-from-concentrate ("NFC") juice. The present disclosure provides a system and method for preparing an NFC juice (in particular, orange juice) that has reduced microbial load and increased shelf stability. The NFC juice made according to the methods of the present disclosure exhibits a taste profile comparable to freshly squeezed non-pasteurized orange juice and a microbial load comparable to pasteurized NFC orange juice.

The term "beverage" is used here to refer to any liquid suitable for human consumption. Examples of beverages include fruit juices, vegetable juices, liquid dairy products (e.g., milk), fermented liquid dairy products (e.g., buttermilk), steeped liquids or extracts (e.g., tea, coffee), fermented liquids (e.g., beer, wine, and the like), broth (e.g., vegetable broth, meat or bone-based broths, mushroom broth, and the like), etc.

The term "juice" is used here to refer to a liquid obtained from a fruit, vegetable, or other plant part (e.g., leaves, roots, tubers, and the like). Juice may be obtained, for example, by pressing or squeezing the fruit, vegetable, or other plant part. Juice may include solids from the fruit, vegetable, or other plant part.

The terms "raw beverage" and "raw juice" are used in this disclosure to describe a beverage or juice that has not been further processed after obtaining the beverage or juice to concentrate the beverage or juice or to remove or kill pathogens. For example, the beverage or juice has not been heated (e.g., pasteurized) or radiated.

The term "sugar" is used here to refer to monosaccharides and disaccharides, such as glucose, fructose, sucrose, and the like.

The term "cross-flow" is used here to refer to a filtration mode where a fluid is flown across the surface of a filter membrane, and where components larger than the size cut-off of the filter membrane remain on the retentate side and components smaller than the size cut-off may flow through the membrane to the permeate side. A continuous flow of fluid across the membrane may flush away material on the retentate side.

The term "direct flow" is used here to refer to a filtration mode where fluid is flown into a filter, such as a cartridge filter, and where components larger than the size cut-off of the filter media remain on the upstream side of the filter and components smaller than the size cut-off may flow through the filter media to the downstream side. A direct flow filter is sometimes referred to as a dead-end filter. A direct flow filter may be cleaned or flushed in a cleaning or flushing cycle where flow through the filter is reversed.

The terms "pasteurize" and "pasteurization" are used here to refer to a heat treatment to eliminate pathogens in a product, typically a liquid food product. During pasteurization the product is heated to an elevated temperature, such as at least 60° C. or at least 70° C., for a set period of time ranging from a number of seconds to several minutes. The specific temperature and time depend on the type of product, the pathogens of interest, and the desired rate of reduction in microbial load.

The term "log reduction" is used here to refer to the reduction in the number of microbes in a product given as a $\log_{10}$ reading. For example, a 5-log reduction is used to mean a 100,000-fold reduction. Log reduction may be determined using any suitable method, such as a microbial culture test.

The terms "microbe" and "pathogen" are used interchangeably, and both refer broadly to bacteria, yeasts, and molds. Examples of microbes and pathogens include spoilage pathogens, such as spoilage bacteria (e.g., *Acetobacter, Alicyclobacillus, Bacillus, Gluconobacter, Lactobacillus, Leuconostoc, Zymomonas*, and *Zymobacter*), yeasts (e.g., *Pichia, Candida, Saccharomyces*, and *Rhodotorula*), and molds (e.g., *Pichia, Candida, Saccharomyces*, and *Rhodotorula*), and disease-causing pathogens (e.g., *E. coli, Listeria, Salmonella*, etc.)

The term "substantially" as used here has the same meaning as "significantly," and can be understood to modify the term that follows by at least about 75%, at least about 90%, at least about 95%, or at least about 98%. The term "not substantially" as used here has the same meaning as "not significantly," and can be understood to have the inverse meaning of "substantially," i.e., modifying the term that follows by not more than 25%, not more than 10%, not more than 5%, or not more than 2%.

The term "about" is used here in conjunction with numeric values to include normal variations in measurements as expected by persons skilled in the art, and is understood have the same meaning as "approximately" and to cover a typical margin of error, such as ±5% of the stated value.

Terms such as "a," "an," and "the" are not intended to refer to only a singular entity, but include the general class of which a specific example may be used for illustration.

The terms "a," "an," and "the" are used interchangeably with the term "at least one." The phrases "at least one of" and "comprises at least one of" followed by a list refers to any one of the items in the list and any combination of two or more items in the list.

As used here, the term "or" is generally employed in its usual sense including "and/or" unless the content clearly dictates otherwise. The term "and/or" means one or all of the listed elements or a combination of any two or more of the listed elements.

The recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" or "at least" a particular value, that value is included within the range.

The words "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

According to an embodiment, a system and method for filtering beverages, such as fruit or vegetable juice, are provided. In particular, the system and method may be suitable for filtering orange juice and for producing an NFC juice. The system and method utilize filtration, and heating of only a part of the beverage, to provide a desired log reduction of pathogens in the beverage. The final product is a treated beverage that may exhibit a taste profile comparable to freshly squeezed non-pasteurized beverage. The treated beverage may have a microbial load comparable to pasteurized NFC orange juice. The system and method are capable of producing a beverage with improved quality and increased shelf-life, as compared to similar beverages processed with conventional methods.

The United States Food and Drug Administration ("FDA") regulates the processing of juice using Hazard Analysis and Critical Control Points ("HACCP") principles. Among other things, the FDA has implemented a 5-log pathogen reduction performance standard, meaning that producers must treat the juice to accomplish a 5-log or 100,000 fold reduction in the number of microorganisms. The producers may use control measures that have been shown to be effective in reducing the number of microorganisms, and must demonstrate the efficacy of the reduction, for example by regular testing.

The treatment of orange juice in particular is known to be challenging due to, at least in part, the high content of both suspended and dissolved solids and of heat-sensitive compounds including flavor compounds, vitamins, flavonoids, and other phytonutrients. Known treatments that are used to reduce the microbial load of orange juice also result in an altered flavor profile and destruction of at least some of the heat-sensitive compounds. The present disclosure provides a system and method that preserves a substantial portion of the heat-sensitive compounds and flavor compounds while reducing the microbial load.

According to an embodiment, the system includes a direct flow filter that is connected to and in fluid communication with (e.g., receives flow from) the permeate side of an ultrafiltration device. The use of a direct flow filter with a suitably selected pore size provides assurance that all or substantially all microbes from the fluid stream are retained and removed. A direct flow filter may remove at least 99%, at least 99.9%, at least 99.99%, at least 99.999%, or at least 99.9999% of the microbes in the fluid stream. In other words, a direct flow filter may be used to sterilize the fluid stream. A direct flow filter is also capable of being tested using a pressure-hold test to verify its integrity. A direct flow filter that passes the test can assure the desired level of microbe removal from the fluid stream. In other words, a benefit of using a direct flow filter is that a certain level or microbial load removal may be assumed from a pressure-hold test.

According to an embodiment, the system and method involve splitting a beverage into two streams (e.g., a solids stream and liquid stream) and treating the two streams separately in a way that assures a certain microbial load reduction (e.g., 5 log or better), where at least one of the streams (e.g., the liquid stream) is treated by a method that does not involve heating or radiation. According to an embodiment, the solids stream may be treated by pasteurization and the liquid stream may be treated by microfiltration. The streams may subsequently be combined.

According to an embodiment, the system and method provide assurance that a 5 log reduction is achieved. For example, the system and method may include an integrity test. An example of an integrity test involves selecting a filter size cut-off that provides the desirable reduction (e.g., 5 log or better) and checking the integrity of the direct flow membrane filter at the end of a membrane sanitization process. The checking may involve two steps: 1) fully wetting the membrane cartridge with clean water, and 2) performing a pressure-hold test or forward diffusion flow test at a given test pressure. As an example, for a 0.2 μm absolute rated cartridge, the pressure-hold-test may involve generating a pressure between a pressurized air source and the wetted membrane at a test pressure of 35 psi, then monitoring at constant volume to detect a pressure decline of less than 3 psi over 10 minutes through the membrane. A diffusion flow test may involve setting the pressure for the same membrane to 35 psi and measuring the volumetric flowrate needed to maintain the pressure steady over the test time, such as below 30 mL/min for a 10 inch and 2.7 inch diameter cartridge filter, and comparing the measured flowrate to a threshold to determine if the cartridge filter is intact (e.g., performs as intended).

In some embodiments, the system of the present disclosure is used to treat a raw beverage. The raw beverage may be fruit juice, such as orange juice. FIG. 1 is a representation of the major components of fruit juice by size. As can be seen, different sizes of components may be present in the juice as suspended solids, colloidal dispersions, and dissolved solids. The largest components, which are present as suspended solids, include pulp, intact cells, starch granules, and yeast cells, at particle sizes of roughly 5 μm and greater. Components that are generally smaller than 1 μm in size and present as colloidal dispersions include bacteria, cell wall fragments, chromoplasts, oil droplets, pectin, hemicelluloses, and proteins. Soluble components having a particle size of less than 0.001 μm include many of the compounds that contribute to the flavor or provide health benefits, such as bioflavonoids, vitamins, organic acids, sugars, and salts.

According to embodiments, the systems and methods of the present disclosure are suitable and beneficial for treatment of beverages, such as raw juice. This is because the systems and methods of the present disclosure are capable of reducing the microbial load of the raw juice without compromising flavor or phytonutrients, such as vitamins, that are present in raw juice. According to embodiments, the raw beverage has not been concentrated or treated to remove or kill pathogens prior to treating in the system of the present disclosure. For example, the raw beverage has not been heated (e.g., pasteurized) or radiated. In some embodiments, the raw beverage has not been chemically treated prior to treating in the system of the present disclosure. According to some embodiments, after obtaining (e.g., juicing, squeezing, pressing, fermenting, etc.) and prior to treatment in the system of the present disclosure, no components have been removed from the raw beverage, including solids, soluble compounds, and microbes. In some embodiments, pectins have not been removed from the raw beverage, e.g., raw juice. In some embodiments, the raw beverage has not been filtered prior to treating in the system of the present disclosure. In some embodiments, the raw beverage has not been centrifuged prior to treating in the system of the present disclosure.

Figure 2A:
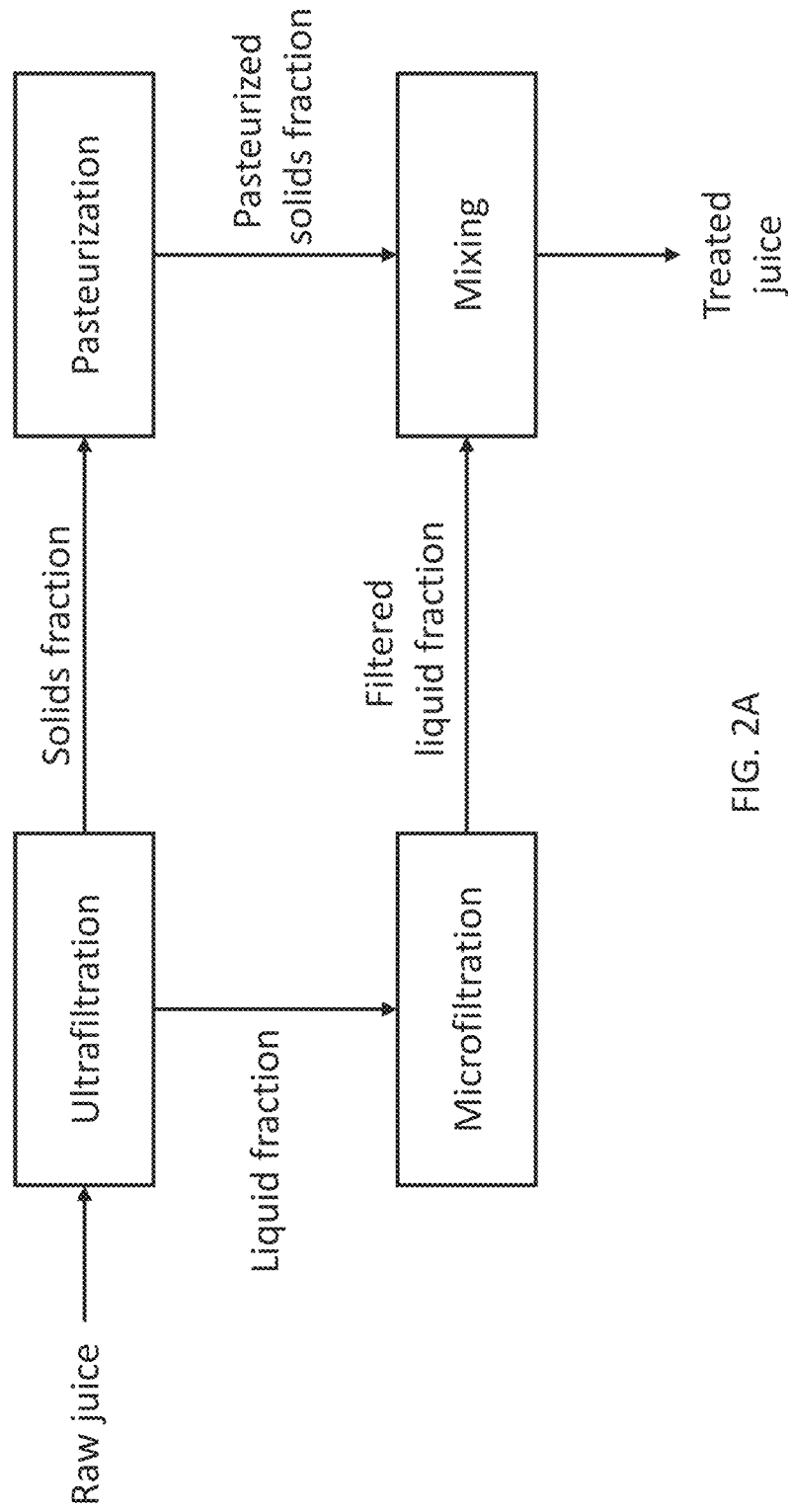
FIG. 2A is a flow diagram of a filtration method according to an embodiment.

The general treatment process is schematically shown in the flow diagram in FIG. 2A. The raw beverage (e.g., juice) may be first split into two streams—a solids fraction and a liquid fraction. The raw beverage may be split into a solids fraction and a liquid fraction using a suitable filtration device, such as an ultrafiltration device. The solids stream may include most, substantially all, or all of the suspended solids of the raw beverage. In some embodiments, the solids fraction has a low water content while still being pumpable. The majority of water, other liquid compounds, and dissolved solids may be contained in the liquid fraction. The weight ratio of the solids fraction and the liquid fraction may be approximately 1:5, 1:6, 1:7, 1:8, 1:9, or 1:10, or any range therebetween (for example, from 1:5 to 1:10).

According to an embodiment, the solids fraction and the liquid fraction are treated separately after separation and before combining the fractions into a final product. Different treatment methods may be used for each fraction. The treatment methods may be selected to be effective at reducing microbial load and to have a minimal impact on the flavor and nutrient profile of the final (combined) product. The solids fraction may be treated to kill pathogens. The treatment of the solids fraction may include, for example, heating (e.g., pasteurization), radiation, or a combination thereof. The liquid fraction may be treated by a method that does not involve heating or radiation. The liquid fraction may be filtered to remove pathogens. The filtration of the liquid fraction may include, for example, microfiltration, resulting in a microfiltered liquid fraction. According to an embodiment, the liquid fraction is not heated or pasteurized. For example, during the method, the temperature of the liquid fraction is never increased above 35° C., above 40° C., above 45° C., or above 50° C. The treated solid and liquid fractions may be combined (e.g., mixed) to produce the final product.

In some embodiments, the solids fraction includes most or substantially all of the suspended solids of the raw beverage. The solids fraction may include most or substantially all of the pectins present in the beverage, e.g., raw juice. The solids fraction may also include naturally occurring enzyme pectin methylesterase. The solids fraction may have a water content of about 50 wt-% or lower, 40 wt-% or lower, 30 wt-% or lower, or 20 wt-% or lower. The solids fraction may have a solids content of 50 wt-% or greater, 60 wt-% or greater, 70 wt-% or greater, or 80 wt-% or greater.

In some embodiments, the liquid fraction includes most of the water and water-soluble compounds (e.g., dissolved solids) of the raw beverage. The liquid fraction may have a water content of about 75 wt-% or greater, 80 wt-% or greater, 85 wt-% or greater, or 90 wt-% or greater. The liquid fraction may have a water content of less than 100 wt-%, such as 99 wt-% or less, 98 wt-% or less, or 95 wt-% or less. The liquid fraction may include dissolved solids in a range of 1 wt-% to 25 wt-%, 5 wt-% to 20 wt-%, 8 wt-% to 20 wt-%, or from 10 wt-% to 15 wt-%. In some embodiments, a majority of the dissolved solids is sugar. The dissolved sugar content of a substance may be estimated using refraction of light, expressed as a Brix reading or degrees Brix (° Bx). One degree of Brix is equivalent to about 1 gram of sucrose in 100 grams of solution. The solids fraction may exhibit a Brix reading of 10 or less, 8 or less, 7 or less, 6 or less, 5 or less, or 4 or less.

The raw beverage may have a water content of about 70 wt-% or greater, 75 wt-% or greater, 80 wt-% or greater, 85 wt-% or greater, or 90 wt-% or greater. The raw beverage may have a water content of up to 98 w-%, 95 wt-%, up to 90 wt-%, up to 85 wt-%, or up to 80 wt-%. The final product (treated, filtered beverage) may have a water content similar to the raw beverage. In other words, the treatment may remove insignificant amounts of either liquid or solids from the raw beverage. For example, the raw beverage may have a first water content and the treated, filtered beverage may have a second water content, and the second water content may be within ±10% of the first water content. In some embodiments, the treated, filtered beverage has a water content of about 70 wt-% or greater, 75 wt-% or greater, 80 wt-% or greater, 85 wt-% or greater, or 90 wt-% or greater. The treated, filtered beverage may have a water content of up to 98 w-%, 95 wt-%, up to 90 wt-%, up to 85 wt-%, or up to 80 wt-%.

Figure 2B:
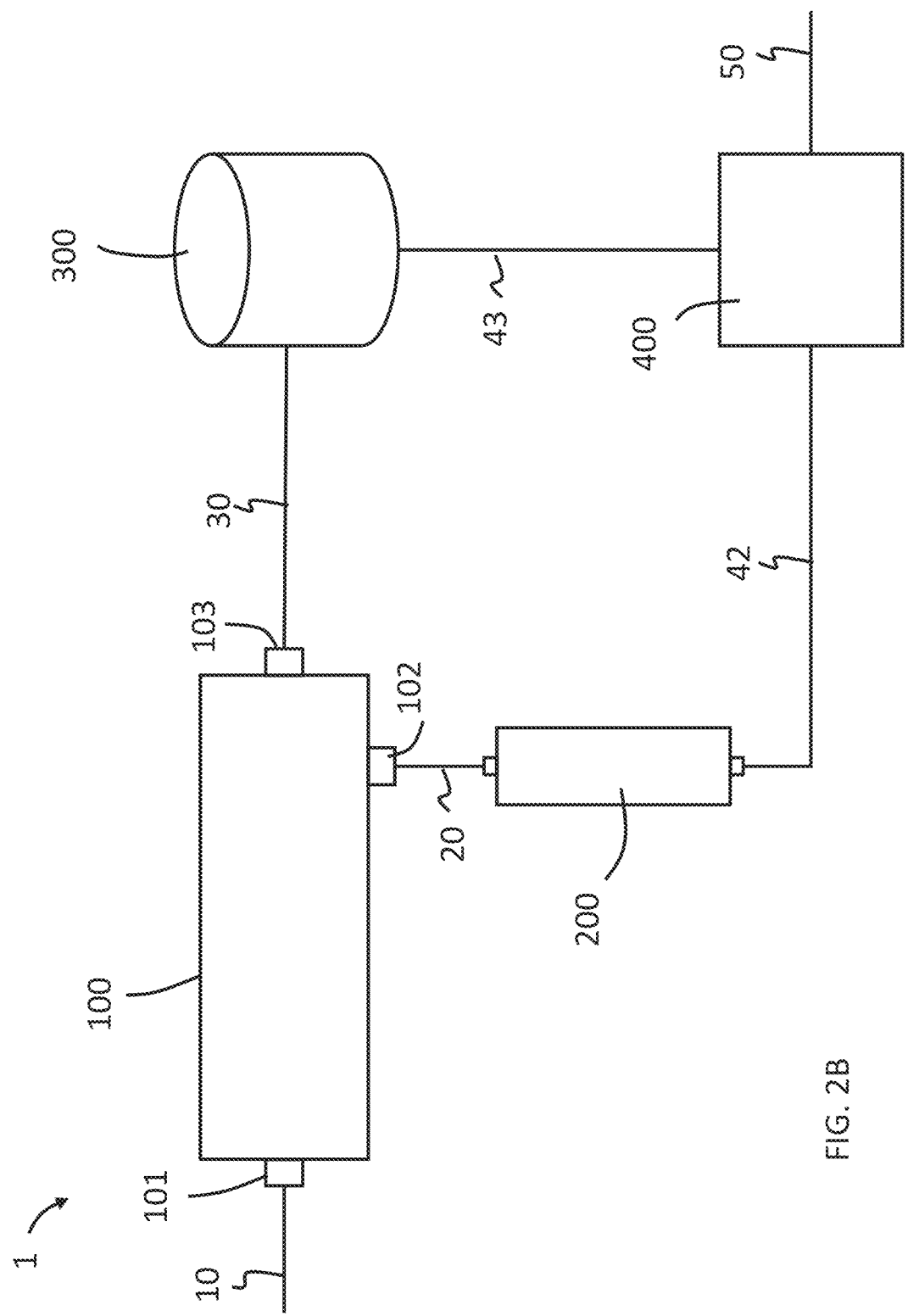
FIG. 2B is a system diagram of a filtration system according to an embodiment.

An exemplary system 1 according to an embodiment of the present disclosure is shown in FIG. 2B. The system 1 may include a source of raw beverage, e.g., raw juice. The source of raw beverage may be, for example, a tank, a juice press, or a feed line. The source of raw beverage may be connected via an input line 10 to the input 101 of an ultrafiltration device 100. The ultrafiltration device 100 may be used to divide the raw beverage into a solids fraction and a liquid fraction. The solids fraction may include the majority of or substantially all of the suspended solids of the raw beverage. The liquid fraction may include water, other liquids, and dissolved solids.

The ultrafiltration device 100 may be arranged in a cross-flow configuration. In cross-flow configuration, a fluid (a juice in this case) is flown across a filter membrane, and components of the fluid that are smaller than a size cut-off of the filter may permeate to the permeate side of the filter, while the rest of the fluid, including components that are larger than the size cut-off, remain on the retentate side and will continue to flow.

Figure 4A:
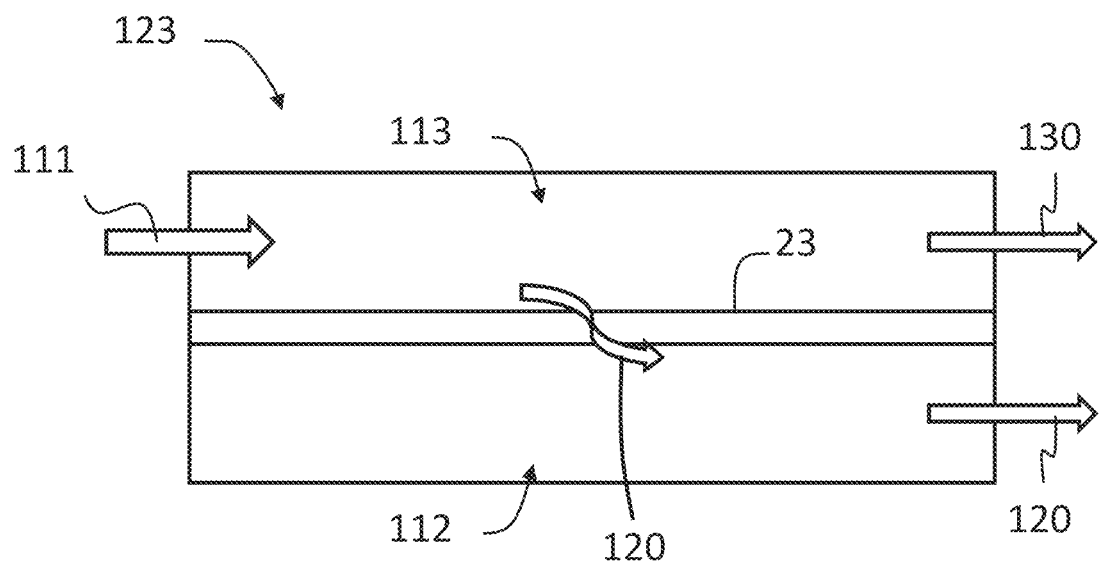
FIGS. 4A and 4B are schematic diagrams of alternative cross-flow ultrafiltration membranes for use in the filtration system of FIGS. 2B and 3B according to an embodiment.
Figure 4B:
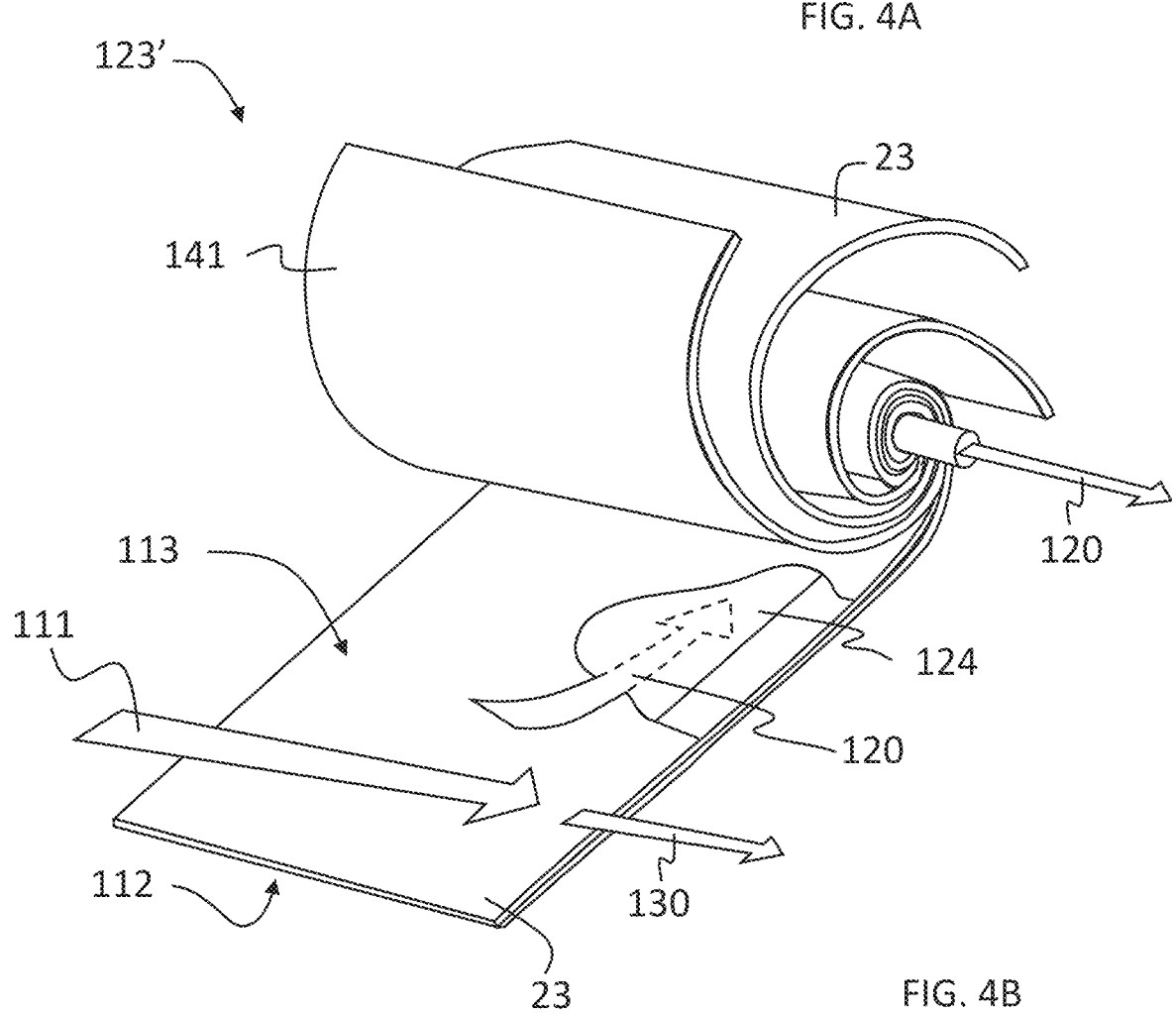

The ultrafiltration device 100 may be set up as a flat (e.g., rectangular) flow device with one or more membranes arranged along a plane, or as a cylindrical device with a wound roll of membrane. An exemplary flat (rectangular) ultrafiltration membrane device 123 is shown schematically in FIG. 4A, and an exemplary peeled-open ultrafiltration membrane 123' of a cylindrical ultrafiltration device is shown schematically in FIG. 4B. The ultrafiltration device 100 may house an ultrafiltration membrane 123, 123' defining a retentate side 113 and a permeate side 112. The ultrafiltration membrane 123, 123' may be a single membrane 23, a manifold of membranes, or a wound roll of separation membranes 23 disposed inside a filter housing or cartridge. The ultrafiltration device 100 may have in inlet that receives and input flow 111 and outlets for output flows of retentate 130 and permeate 120. The separation membrane 23 may be selected to remove (e.g., retain) solid particles or molecules above a certain size cut-off. The layers of separation membranes 23 may be separated by spacers 141. The separation membrane 23 itself may also include a spacer layer 124 to facilitate flow of permeate 120.

The ultrafiltration device may be configured to retain the majority of, substantially all, or all of the suspended solids of the raw beverage on the retentate side of the membrane. The ultrafiltration device may be configured to allow the majority of or substantially all of the flavor and aroma compounds and other small molecules, such as vitamins, of the raw beverage to pass to the permeate side of the membrane. The ultrafiltration membrane may have particle size cut-off defined based on molecular weight. For example, the ultrafiltration membrane may have particle size cut-off selected based on the size of the small molecules desired to stay with the liquid fraction, while larger particles, suspended solids, and microbes stay with the solids fraction. For example, small molecules that are desired to stay in the liquid fraction include sugars (e.g., the molecular weights of most mono- and disaccharides are in the range of 180 to 350 Da (dalton)), flavor compounds, vitamins (e.g., the molecular weights of most B and C vitamins are in the range of 120 to 450 Da), flavonoids (e.g., certain flavonoids have molecular weights in the range of 300 to 700 Da), and/or other phytonutrients. On the other hand, larger particles, such as cell wall fragments and bacteria typically have particle sizes greater than 0.5 μm (expressed in molecular weight, roughly 500 kDa (kilodalton) or greater). The ultrafiltration membrane may have a molecular weight cut-off of 10 kDa or greater, 20 kDa or greater, 40 kDa or greater, 60 kDa or greater, 80 kDa or greater, or 100 kDa or greater. The molecular weight cut-off may be 300 kDa or less, 250 kDa or less, 200 kDa or less, 150 kDa or less, 120 kDa or less, or 100 kDa or less. In some embodiments, the molecular weight cut-off is in the range of 10 kDa to 300 kDa, or from 100 kDa to 200 kDa.

Referring again to FIG. 2B, the separated liquid fraction (permeate 120) exits the ultrafiltration device 100 at outlet 102 and is flown along line 20 to the microfiltration device 200. The microfiltration device 200 may be configured as a direct flow filter. The microfiltration device 200 may house a microfilter selected to retain most, substantially all, or all microbes present in the liquid fraction. The microfilter may define an upstream side and a filtrate side. The microfilter may be a cartridge filter, including a cartridge that houses suitable filter media. Examples of suitable filter media include pleated media and microfiltration membranes. The microfilter may have a size cut-off of 1.2 μm or smaller, 1.1 μm or smaller, 1 μm or smaller, 0.9 μm or smaller, 0.8 μm or smaller, 0.7 μm or smaller, 0.6 μm or smaller, or 0.5 μm or smaller. The microfilter may have a size cut-off of 0.1 μm or greater, 0.2 μm or greater, 0.3 μm or greater, 0.4 μm or greater, or 0.5 μm or greater. In some embodiments, the size cut-off is in the range of 0.2 μm to 1.0 μm. Using a direct flow filter with a suitably selected cut-off allows the permeate (filtered liquid fraction) to be mixed into the final product without additional treatment (e.g., heat or radiation) because the direct flow filter maintains all or substantially all microbes on the upstream side. According to an embodiment, the microfiltration device 200 is configured as a direct flow filter and has a size cut-off of 1.2 μm or smaller, 1.1 μm or smaller, 1 μm or smaller, 0.9 μm or smaller, 0.8 μm or smaller, 0.7 μm or smaller, 0.6 μm or smaller, or 0.5 μm or smaller, and achieves at least 99%, at least 99.9%, at least 99.99%, at least 99.999%, or at least 99.9999% removal of microbes present in the separated liquid fraction. In some embodiments, the microfiltration device 200 is capable of sterilizing the separated liquid fraction.

According to an embodiment, the microfiltered liquid fraction exhibits at least a 5 log reduction in pathogens compared to the raw beverage. In some embodiments, the microfiltered liquid fraction is substantially free of pathogens. According to an embodiment, the microfiltered liquid fraction is substantially free of pathogens without heat treatment, radiation, or both heat and radiation treatment. In particular, according to an embodiment, the liquid fraction is treated without heat treatment, radiation, or both heat and radiation treatment, and is substantially free of pathogens without heat treatment, radiation, or both heat and radiation treatment. Heat treatment is considered to be a treatment where the temperature of the substance is increased to 50° C. or greater. Thus, according to an embodiment, the temperature of the liquid fraction during the process does not reach 50° C. or higher. The liquid fraction may contain a majority of the dissolved solids of the raw beverage (e.g., sugars, flavor compounds, vitamins, flavonoids, and other phytonutrients).

According to an embodiment, the liquid fraction contains a majority of the sugars in the raw beverage. According to an embodiment, the liquid fraction contains 50% or more, 60% or more, 75% or more, 80% or more, 85% or more, 90% or more, or 95% or more of the sugar of the raw beverage. According to an embodiment, the liquid fraction contains a majority of the vitamin C in the raw beverage. According to an embodiment, the liquid fraction has a vitamin C concentration that is 50% or more, 60% or more, 70% or more, 75% or more, 80% or more, or 85% or more of the vitamin C concentration of the raw beverage.

The separated solids fraction (retentate 130) exits the ultrafiltration device 100 at outlet 103 and is flown along line 30 to a treatment device 300. The treatment device 300 is coupled with and configured to receive flow from the retentate side of the ultrafiltration device 100. The treatment device 300 may be, for example, a heater (e.g., a pasteurizer). Other possible devices include, for example, devices capable of radiating the solids fraction with UV, high energy, or particle radiation. In one embodiment, the treatment device 300 includes a pasteurizer. The pasteurizer may include a heated tank or a flow-through heater (for example, heat exchanger). The pasteurizer may be configured to heat the solids fraction to a temperature sufficient to kill pathogens. For example, the pasteurizer may be configured to heat the solids fraction to about 60° C. or greater, 65° C. or greater, or 70° C. or greater. The pasteurizer may be configured to heat the solids fraction to about 95° C. or lower, 90° C. or lower, 85° C. or lower, 80° C. or lower, 75° C. or lower, or 70° C. or lower. The pasteurizer may be configured to hold the temperature of the solids fraction at the pasteurization temperature for a set period of time. For example, the pasteurizer may be configured to maintain the solids fraction at the pasteurization temperature for 10 s or longer, 30 s or longer, 1 min or longer, or 2 min or longer. The pasteurizer may be configured to maintain the solids fraction at the pasteurization temperature for 15 min or less, 10 min or less, 5 min or less, or 2 min or less. According to an embodiment, there is no flow from the microfiltration device 200 to the treatment device 300.

According to an embodiment, the treated (e.g., pasteurized) solids fraction exhibits at least a 5 log reduction in pathogens compared to the raw beverage. In some embodiments, the treated (e.g., pasteurized) solids fraction is substantially free of pathogens.

The microfiltered liquid fraction may be flown from the microfiltration device 200 via line 42 to a mixer 400 and the treated solids fraction may be flown from the treatment device 300 via line 43 to the mixer 400. The mixer 400 may be coupled with and configured to receive flow from the filtrated side of the microfiltration device 200, and the treatment device 300. The mixer 400 may include a mixing vessel or may be an inline mixer. The final product (treated beverage, e.g., juice) may be led out of the system 1 via output line 50. According to an embodiment, the final product exhibits at least a 5 log reduction in pathogens compared to the raw beverage. In some embodiments, the final product is substantially free of pathogens.

In some embodiments, the microfiltered liquid fraction is not mixed with the treated solids fraction. Rather, the microfiltered liquid fraction may be recovered and optionally packaged to provide a beverage that comprises a filtered liquid fraction of a raw juice. According to an embodiment, the beverage product may be a filtered liquid fraction made by filtering a raw beverage, e.g., raw juice, using a cross-flow ultrafiltration device to separate a solids fraction from a liquid fraction; and microfiltering the liquid fraction through a microfilter having a size cut-off of 1.2 µm or smaller, 1.1 µm or smaller, 1.0 µm or smaller, 0.9 µm or smaller, 0.8 µm or smaller, 0.7 µm or smaller, 0.6 µm or smaller, or 0.5 µm or smaller; and/or 0.1 µm or greater, 0.2 µm or greater, 0.3 µm or greater, 0.4 µm or greater, or 0.5 µm or greater, to produce a microfiltered liquid fraction. The filtered liquid fraction has been found to retain at least some or most of the color of the raw beverage (e.g., raw juice) while being mostly or completely transparent (e.g., without turbidity). The filtered liquid fraction made from a fruit juice has also been found to retain most of the fragrance and at least some of the flavor of the raw beverage (e.g., raw juice).

Figure 3A:
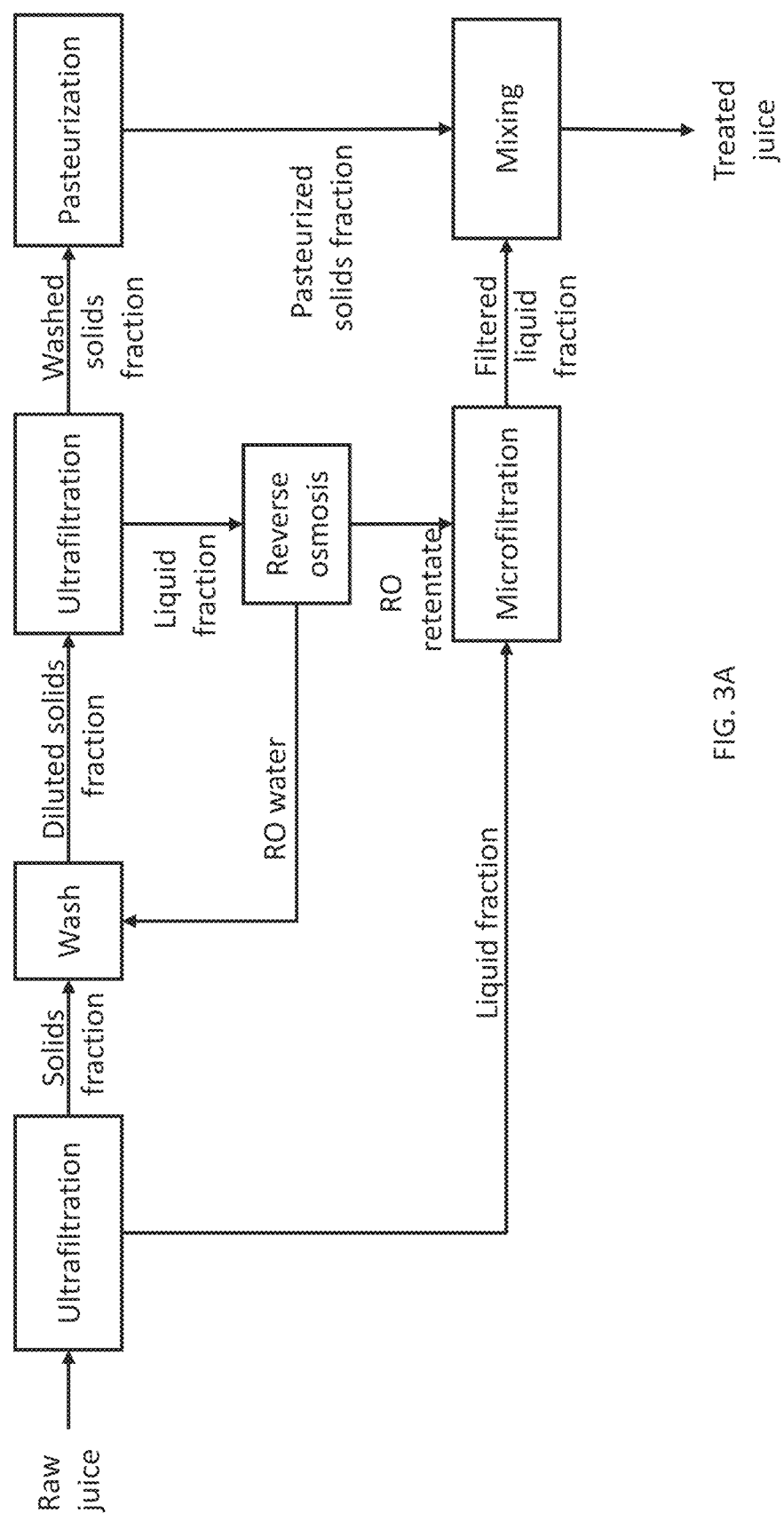
FIG. 3A is a flow diagram of a filtration method according to an embodiment.
Figure 3B:
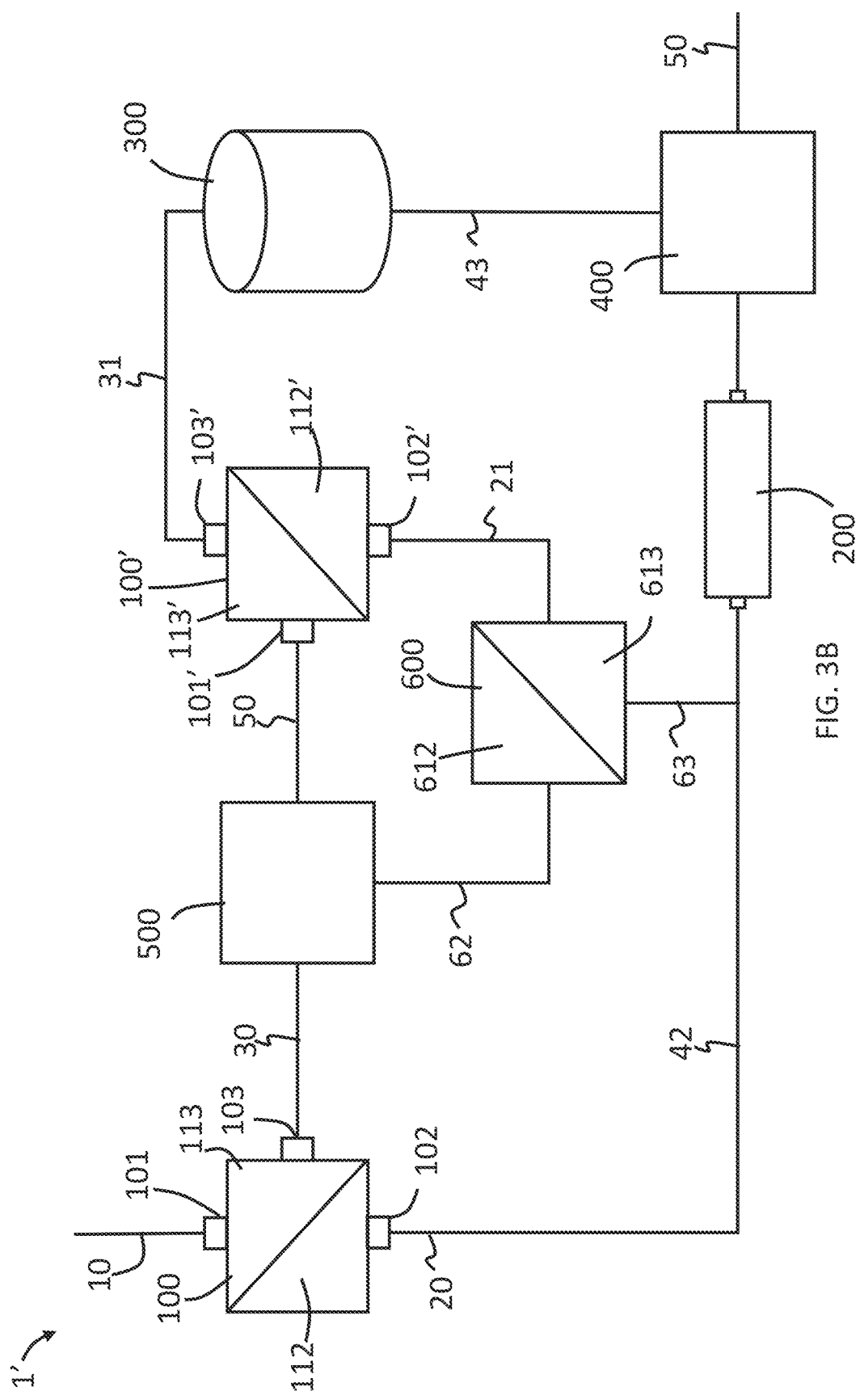
FIG. 3B is a system diagram of a filtration system according to an embodiment.

According to an embodiment, the method further includes utilizing water recirculation to help wash more sugars and other small molecules from the solids fraction. A schematic flow diagram of such as process is shown in FIG. 3A, and the system diagram of the system configured for the process is shown in FIG. 3B. As can be seen in FIG. 3A, the process is otherwise similar to that described with reference to FIG. 2A, but in addition, reverse osmosis ("RO") is used to separate water from the liquid fraction, and the RO water is returned back into a mixing tank and mixed with a solids fraction. The added water dilutes the sugars and small molecules present in the solids fraction, and helps remove them in a subsequent ultrafiltration step.

As above, the separated solids fraction (retentate 130) exits the ultrafiltration device 100 at outlet 103 and is flown along line 30. However, instead of being directed to the treatment device 300, the solids fraction is first mixed with RO water in mixing tank 500 and then ultrafiltered again in ultrafiltration device 100'. This cycle may be repeated more than once until a desired sugar content in the solids fraction is reached. Monitoring the sugar content in the solids fraction may be used as an indicator of the separation efficiency of separating sugars and small molecules from the solids fraction. The treatment device 300 is coupled with and configured to receive flow from the retentate side of the ultrafiltration device 100'. The treatment device 300 may be as described above with regard to FIGS. 2A and 2B. The RO retentate (liquid fraction with some water removed) is combined with the initial liquid fraction stream and is microfiltered to produce the filtered liquid fraction. The washed solids fraction, which includes less sugars and small molecules than the initial solids fraction is treated (e.g., pasteurized). The treated (e.g., pasteurized) solids fraction is combined with the microfiltered liquid fraction to produce treated juice.

The system 1' shown in FIG. 3B includes the components of the system 1 shown in FIG. 2B and additional includes the components of the water circulation loop. In particular, FIG. 3B includes a RO membrane filter 600 in fluid communication with (e.g., receiving flow from) the permeate side 112' of an ultrafiltration device 100' through outlet 102' and via line 21. The RO membrane filter 600 has a permeate side 612 that is in fluid communication with (e.g., delivers flow to) a mixing tank 500 (e.g., the wash tank) via line 62. The mixing tank 500 also receives flow from the retentate side (outlet 103) of the ultrafiltration device 100 along line 30.

The mixing tank 500 is in fluid communication with (e.g., delivers flow to) the ultrafiltration device 100' via line 50. The RO membrane filter 600 further has a retentate side 613 that is in fluid communication with (e.g., delivers flow to) the microfilter 200 via line 63. The retentate side 113' of ultrafiltration device 100' delivers flow to the treatment device 300 through outlet 103' and along line 31.

According to an embodiment, by using a water recirculation loop, the relative sugar content in the liquid fraction may be even higher. For example, the liquid fraction may contain 85% or more, 90% or more, 95% or more, or 98% or more of the sugar of the raw beverage. According to an embodiment, the liquid fraction has a vitamin C concentration that is 85% or more, 90% or more, 95% or more, or 98% or more of the vitamin C of the raw beverage.

In some embodiments, the beverage includes the filtered liquid fraction made by the methods described herein and having a suspended solids content of less than 5 wt-% or less than 2 wt-%. In some embodiments, the beverage consists essentially the pasteurized solids fraction and the microfiltered liquid fraction. In some embodiments, the beverage consists of the pasteurized solids fraction and the microfiltered liquid fraction. In some embodiments, the beverage consists essentially of the filtered liquid fraction. In some embodiments, the beverage includes sugars and flavor compounds that have not been heat treated or radiation treated, and the beverage has a microbial load of less than 10 CFU/g (colony forming units per gram). In some embodiments, the beverage includes small molecules having molecular weight below 1000 Da that have not been heat treated or radiation treated, and has a microbial load of less than 10 CFU/g. The small molecules may comprise sugars, flavor compounds, and vitamins. In some embodiments, the beverage or consists of the pasteurized solids fraction and the microfiltered liquid fraction. In other words, in some embodiments the filtered liquid fraction has not been combined with the solids fraction.

The following is a list of exemplary aspects of the articles according to the present disclosure.

According to aspect 1, a method for preparing a filtered beverage, e.g., fruit juice, comprises filtering a raw beverage, e.g., raw juice, using a cross-flow ultrafiltration device to produce a solids fraction and a liquid fraction; heating the solids fraction to a temperature of 60° C. or greater, 65° C. or greater, or 70° C. or greater, and/or to 95° C. or lower, 90° C. or lower, 85° C. or lower, 80° C. or lower, 75° C. or lower, or 70° C. or lower, to produce a pasteurized solids fraction; microfiltering the liquid fraction through a microfilter having a size cut-off of 1.2 μm or smaller, 1.1 μm or smaller, 1.0 μm or smaller, 0.9 μm or smaller, 0.8 μm or smaller, 0.7 μm or smaller, 0.6 μm or smaller, or 0.5 μm or smaller; and/or 0.1 μm or greater, 0.2 μm or greater, 0.3 μm or greater, 0.4 μm or greater, or 0.5 μm or greater, to produce a microfiltered liquid fraction; and combining the pasteurized solids fraction and the microfiltered liquid fraction to result in the filtered beverage, e.g., filtered juice.

Aspect 2 is the method aspect 1, wherein the beverage comprises raw juice.

Aspect 3 is the method of aspect 1 or 2, wherein the raw beverage, e.g., raw juice, has a water content of 70 wt-% or greater, 75 wt-% or greater, 80 wt-% or greater, 85 wt-% or greater, or 90 wt-% or greater, and/or up to 95 wt-%, up to 90 wt-%, up to 85 wt-%, or up to 80 wt-%, and the filtered beverage, e.g., filtered juice, has a water content of 70 wt-% or greater, 75 wt-% or greater, 80 wt-% or greater, 85 wt-% or greater, or 90 wt-% or greater, and/or up to 95 wt-%, up to 90 wt-%, up to 85 wt-%, or up to 80 wt-%.

Aspect 4 is the method of any one of the preceding aspects, wherein the raw beverage, e.g., raw juice, has a first water content and the filtered beverage, e.g., filtered juice, has a second water content, and wherein the second water content is within ±10% of the first water content.

Aspect 5 is the method of any one of the preceding aspects, wherein the solids fraction has a water content of 50 wt-% or lower, 40 wt-% or lower, 30 wt-% or lower, or 20 wt-% or lower.

Aspect 6 is the method of any one of the preceding aspects, wherein the solids fraction has a solids content of 40 wt-% to 90 wt-%, or 50 wt-% or greater, 60 wt-% or greater, 70 wt-% or greater, or 80 wt-% or greater, and up to 90 wt-%.

Aspect 7 is the method of any one of the preceding aspects, wherein the liquid fraction comprises from 8 wt-% to 20 wt-% dissolved solids.

Aspect 8 is the method of any one of the preceding aspects, wherein the liquid fraction has a vitamin C concentration that is 75% or more of a vitamin C concentration of the raw beverage.

Aspect 9 is the method of any one of the preceding aspects, wherein the cross-flow ultrafiltration device comprises a membrane having a size cut-off of 10 kDa or greater, 20 kDa or greater, 40 kDa or greater, 60 kDa or greater, 80 kDa or greater, or 100 kDa or greater, and/or wherein the molecular weight cut-off is 300 kDa or less, 250 kDa or less, 200 kDa or less, 150 kDa or less, 120 kDa or less, or 100 kDa or less. In some embodiments, the molecular weight cut-off is in the range of 10 kDa to 300 kDa, or from 100 kDa to 200 kDa.

Aspect 10 is the method of any one of the preceding aspects, wherein the microfilter is arranged as a direct flow filter.

Aspect 11 is the method of any one of the preceding aspects, wherein the microfilter has a size cut-off of 0.1 μm to 1.0 μm, from 0.1 μm to 0.5 μm, or from 0.2 μm to 0.3 μm.

Aspect 12 is the method of any one of the preceding aspects, wherein the liquid fraction has a first microbial content and the microfiltered liquid fraction has a second microbial content, and wherein the second microbial content is at least 5-log reduced from the first microbial content.

Aspect 13 is the method of any one of the preceding aspects, wherein the microfiltering removes at least 99%, at least 99.9%, at least 99.99%, at least 99.999%, or at least 99.9999% of microbes in the liquid fraction.

Aspect 14 is the method of any one of the preceding aspects, wherein the microfiltering sterilizes the liquid fraction.

Aspect 15 is the method of any one of the preceding aspects, wherein the liquid fraction has a first microbial content and the microfiltered liquid fraction has a second microbial content, and wherein the second microbial content is at least 5-log reduced from the first microbial content.

Aspect 16 is the method of any one of the preceding aspects, wherein the raw beverage, e.g., raw juice, has a raw beverage microbial content and the filtered beverage, e.g., filtered juice, has a final microbial content, and wherein the final microbial content is at least 5-log reduced from the raw beverage, e.g., raw juice, microbial content.

Aspect 17 is the method of any one of the preceding aspects, wherein the method does not include a concentration step where concentration is done by evaporation.

Aspect 18 is the method of any one of the preceding aspects, wherein the method does not include a step of concentrating the liquid fraction.

Aspect 19 is the method of any one of the preceding aspects, wherein the method does not include heat treatment of the liquid fraction.

Aspect 20 is the method of any one of the preceding aspects, wherein the method does not include radiation treatment of the liquid fraction.

Aspect 21 is the method of any one of the preceding aspects, wherein the combining occurs immediately after the microfiltering. According to a preferred aspect, there is no flow from the microfiltration device to the treatment device.

Aspect 22 is the method of any one of the preceding aspects, further comprising an integrity test comprising testing the integrity of a filter membrane of the microfilter.

Aspect 23 is the method of aspect 22, wherein the integrity test comprises performing a pressure-hold test or forward diffusion flow test at a given test pressure.

Aspect 24 is a filtration system comprising an ultrafiltration device comprising an ultrafiltration retentate side and an ultrafiltration permeate side, the ultrafiltration device being configured in cross-flow mode; a heater coupled with and configured to receive flow from the ultrafiltration retentate side and comprising an output line; a microfilter coupled with and configured to receive flow from the ultrafiltration permeate side, the microfilter comprising a microfiltration upstream side and microfiltration filtrate side and having a particle size cut-off of 1 µm or smaller, the microfilter being configured in direct flow filtration mode; and a mixer coupled with and configured to receive flow from the heater output line and the microfiltration filtrate side.

Aspect 25 is the filtration system of aspect 24, wherein the cross-flow ultrafiltration device comprises a membrane having a size cut-off of 10 kDa or greater, 20 kDa or greater, 40 kDa or greater, 60 kDa or greater, 80 kDa or greater, or 100 kDa or greater, and/or wherein the molecular weight cut-off is 300 kDa or less, 250 kDa or less, 200 kDa or less, 150 kDa or less, 120 kDa or less, or 100 kDa or less. In some embodiments, the molecular weight cut-off is in the range of 10 kDa to 300 kDa, or from 100 kDa to 200 kDa.

Aspect 26 is the filtration system of aspect 24 or 25, wherein the microfilter has a size cut-off of 1.2 µm or smaller, 1.1 µm or smaller, 1 µm or smaller, 0.9 µm or smaller, 0.8 µm or smaller, 0.7 µm or smaller, 0.6 µm or smaller, or 0.5 µm or smaller, and/or wherein the microfilter has a size cut-off of 0.1 µm or greater, 0.2 µm or greater, 0.3 µm or greater, 0.4 µm or greater, or 0.5 µm or greater. In some embodiments, the size cut-off is in the range of 0.2 µm to 1.0 µm.

Aspect 27 is the filtration system of any one of aspects 24 to 26, further comprising a second ultrafiltration device comprising a second ultrafiltration retentate side and a second ultrafiltration permeate side, the second ultrafiltration device being configured in cross-flow mode; a reverse osmosis membrane filter coupled with and configured to receive flow from the second ultrafiltration permeate side, the reverse osmosis membrane filter comprising a reverse osmosis permeate side; and a second mixer coupled with and configured to receive flow from the first ultrafiltration retentate side and the reverse osmosis permeate side, the heater being configured to receive flow from the second ultrafiltration retentate side. The reverse osmosis membrane filter further comprises a retentate side that is coupled with and configured to deliver flow to the microfilter.

Aspect 28 is a beverage comprising a microfiltered liquid fraction made by the method of any one of aspects 1 to 23.

Aspect 29 is the beverage of aspect 28 having a suspended solids content of less than 5 wt-% or less than 2 wt-%.

Aspect 30 is the beverage of aspect 28 consisting essentially of the filtered liquid fraction.

Aspect 31 is a beverage comprising a microfiltered liquid fraction made by filtering a raw beverage, e.g., raw juice, using a cross-flow ultrafiltration device to produce a solids fraction and a liquid fraction; and microfiltering the liquid fraction using a direct-flow microfilter having a size cut-off of 1.2 µm or smaller, 1.1 µm or smaller, 1.0 µm or smaller, 0.9 µm or smaller, 0.8 µm or smaller, 0.7 µm or smaller, 0.6 µm or smaller, or 0.5 µm or smaller; and/or 0.1 µm or greater, 0.2 µm or greater, 0.3 µm or greater, 0.4 µm or greater, or 0.5 µm or greater, to produce the microfiltered liquid fraction.

Aspect 32 is the beverage of aspect 31, wherein the beverage comprises small molecules having molecular weight below 1000 Da that have not been heat treated or radiation treated, and wherein the beverage has a microbial load of less than 10 CFU/g. The small molecules may comprise sugars, flavor compounds, and vitamins.

Aspect 33 is a beverage made by the method of any one of aspects 1 to 23 and consisting of the pasteurized solids fraction and the microfiltered liquid fraction.

Example

A filtration system according to the present disclosure was tested for treating raw orange juice. The raw juice was unpasteurized, fresh-squeezed orange juice with an initial Brix reading of 11.1. The treatment system included an ultrafiltration cross-flow filter that was used to separate a solids fraction and a liquid fraction; a microfilter for filtering the liquid fraction, and a pasteurizer for pasteurizing the solids fraction. The juice was flown through the system using a pump at 190 L/min. The system was set up as shown in FIGS. 3A and 3B.

The ultrafiltration cross-flow filter included a rectangular flat sheet polyether sulfone (PES) membrane with adjustable spacers to create flow channels. During operation, most of the flow passed over the flow channels and returned to the pump. The test was performed on 48 kg raw orange juice, separated into 34 kg permeate and 14 kg retentate. The liquid fraction that permeated the membrane was collected at a rate of 0.4 L/min. The molecular weight cutoff of the ultrafiltration membrane was 150 kDa, corresponding to a 15 nm nominal pore size.

The microfilter was a direct flow filter (product number 1C230101-82 available from Donaldson Company, Inc. in Minneapolis, Minn.) fitted with a PES-WN 10-inch, 0.2 µm filter.

Reverse Osmosis was performed using a cross-flow filter with an RO membrane having 100 Da molecular weight cut-off.

The initial sugar content (Brix reading) of the retentate was 12.8. The sugar content at line 31 ("low sugar retentate"), and line 21 (wash cycle permeate) was monitored after 1 cycle, 2 cycles, 3 cycles, and 4 cycles of washing with RO water. The sugar content was estimated using a Brix refractometer (ATAGO 3810 PAL-1, available from Atago Co. Ltd. in Tokyo, Japan). The Brix readings are shown in TABLE 1 below.

TABLE 1

Brix analysis.

|  | Retentate Brix (Line 31) | Wash Cycle Permeate Brix (Line 21) |
|---|---|---|
| Cycle #1 | 7.0 | 5.8 |
| Cycle #2 | 4.4 | 3.2 |
| Cycle #3 | 3.2 | 1.7 |
| Cycle #4 | 2.2 | 0.9 |

*below detection threshold

It was observed that the sugar content (Brix reading) of the retentate could be reduced from 12.8 to 2.2 by performing a wash with RO water. This further reduces the amount of sugar being exposed to pasteurization. This may further reduce off-flavors in the final product.

The permeate from the ultrafiltration cross-flow filter (line 42 in FIG. 3B) was collected into an aseptic clear plastic bag fitted with a sampling port. The permeate was observed to be substantially clear with a light orange color, and to have the smell and taste of oranges but somewhat muted. The permeate was found to have a Brix reading of 10.9.

The permeate was further filtered using the direct flow microfilter. The filtered permeate was analyzed for microbial content. The results, compared to the analysis of the raw juice, are shown in TABLE 2 below.

TABLE 2

Sample analysis.

|  | Filtered Permeate | Unpasteurized Raw Juice |
|---|---|---|
| Lactic Acid Bacteria | <10 CFU/g* | 250 CFU/g |
| Aerobic Plate Count | <10 CFU/g* | 140 CFU/g |
| Yeast | <10 CFU/g* | 250 CFU/g |
| Mold | <10 CFU/g* | <10 CFU/g* |

*below detection threshold

The microbial analysis was repeated again after storing the samples for one month and for three months at a refrigerated temperature of 40° F. The one-month results are shown in TABLE 3A below, and the 3-month results are shown in TABLE 3B.

TABLE 3A

Sample analysis after one month of storage.

|  | Filtered Permeate | Unpasteurized Raw Juice |
|---|---|---|
| Lactic Acid Bacteria | <10 CFU/g* | 50 CFU/g |
| Aerobic Plate Count | <10 CFU/g* | 200,000 CFU/g |
| Yeast | <10 CFU/g* | 150,000 CFU/g |
| Mold | <10 CFU/g* | <10 CFU/g* |

*below detection threshold

TABLE 3B

Sample analysis after three months of storage.

|  | Filtered Permeate | Unpasteurized Raw Juice |
|---|---|---|
| Lactic Acid Bacteria | <10 CFU/g* | <10 CFU/g |
| Aerobic Plate Count | <10 CFU/g* | 160,000 CFU/g |
| Yeast | <10 CFU/g* | 720,000 CFU/g |
| Mold | <10 CFU/g* | 110 CFU/g |

*below detection threshold

The retentate from the ultrafiltration cross-flow filter formed the solids fraction. The solids fraction was found to have a very bright color and strong fragrance but a weak, slightly bitter flavor. The retentate was pasteurized in a pasteurization loop at a temperature of 90° C. for 10 min. The pasteurized retentate was cooled to 60° C. and bagged. The pasteurized retentate maintained its color and fragrance.

The pasteurized retentate was mixed with the filtered permeate to produce the final product. The final filtered product was tested in a blind taste test against the original raw juice. The effect of the processing was found to be negligible.

All references and publications cited herein are expressly incorporated herein by reference in their entirety into this disclosure, except to the extent they may directly contradict this disclosure. Although specific embodiments have been illustrated and described herein, it will be appreciated by those of ordinary skill in the art that a variety of alternate and/or equivalent implementations can be substituted for the specific embodiments shown and described without departing from the scope of the present disclosure. It should be understood that this disclosure is not intended to be unduly limited by the illustrative embodiments and examples set forth herein and that such examples and embodiments are presented by way of example only with the scope of the disclosure intended to be limited only by the claims set forth here.

The invention claimed is:

1. A method for preparing a filtered beverage, the method comprising:
   filtering a raw beverage using cross-flow ultrafiltration to produce a solids fraction and a liquid fraction, the raw beverage having a first sugar concentration and the solids fraction having a second sugar concentration;
   mixing reverse osmosis water with the solids fraction from the cross-flow ultrafiltration to produce a diluted solids fraction;
   filtering the diluted solids fraction using cross-flow ultrafiltration to produce a washed solids fraction and a second liquid fraction, the washed solids fraction having a third sugar concentration that is about 55% or less of the second sugar concentration;
   separating the reverse osmosis water from the second liquid fraction using reverse osmosis and forming a reverse osmosis retentate;
   heating the washed solids fraction to a temperature of 60° C. or greater to produce a pasteurized solids fraction;
   microfiltering the liquid fraction and the reverse osmosis retentate through a microfilter having a size cut-off of 0.1 µm to 1 µm to produce a microfiltered liquid fraction, the microfilter being configured in direct flow filtration mode; and
   combining the pasteurized solids fraction and the microfiltered liquid fraction to result in the filtered beverage,
   wherein during the method, the liquid fraction does not reach a temperature of 50° C. or higher.

2. The method of claim 1, wherein the beverage comprises raw juice.

3. The method of claim 1, wherein the raw beverage has a water content of 80 wt-% to 95 wt-% and the filtered beverage has a water content of 80 wt-% to 95 wt-%.

4. The method of claim 1, wherein the raw beverage has a first water content and the filtered beverage has a second water content, and wherein the second water content is within ±10% of the first water content.

5. The method of claim 1, wherein the liquid fraction has a vitamin C concentration that is 75% or more of a vitamin C concentration of the raw beverage.

6. The method of claim 1, wherein the cross-flow ultrafiltration comprises filtration using a membrane having a size cut-off from 10 kDa to 300 kDa.

7. The method of claim 1, wherein the liquid fraction comprises from 8 wt-% to 20 wt-% dissolved solids.

8. The method of claim 1, wherein the solids fraction comprises from 40 wt-% to 90 wt-% solids.

9. The method of claim 1, wherein the liquid fraction has a first microbial content and the microfiltered liquid fraction has a second microbial content, and wherein the second microbial content is at least 5-log reduced from the first microbial content.

10. The method of claim 1, wherein the raw beverage has a raw beverage microbial content and the filtered beverage has a final microbial content, and wherein the final microbial content is at least 5-log reduced from the raw beverage microbial content.

11. The method of claim 1, wherein the method does not include concentrating a portion of the raw beverage by evaporation.

12. The method of claim 1, wherein the method does not include a step of concentrating the liquid fraction.

13. The method of claim 1, wherein the combining occurs immediately after the microfiltering.

14. The method of claim 1, wherein the method does not include heat treatment of the liquid fraction.

15. The method of claim 1, wherein the method does not include radiation treatment of the liquid fraction.

16. The method of claim 1 further comprising an integrity test comprising performing a pressure-hold test to evaluate the integrity of a filter membrane of the microfilter.

17. The method of claim 1 further comprising an integrity test comprising performing a forward diffusion flow test at a given test pressure to evaluate the integrity of a filter membrane of the microfilter.

18. The method of claim 1, wherein the raw beverage has a raw beverage microbial content and the filtered beverage has a final microbial content, the method further comprising an integrity test comprising testing the integrity of a filter membrane of the microfilter by a pressure-hold test or forward diffusion flow test at a test pressure, wherein the integrity test assures 5-log microbial reduction of the final microbial content compared to the raw beverage microbial content.

19. The method of claim 18, wherein the integrity test comprises the pressure-hold test and assuring 5-log microbial reduction based on the pressure-hold test.

* * * * *